United States Patent
Hashimoto

(10) Patent No.: US 12,408,986 B2
(45) Date of Patent: Sep. 9, 2025

(54) DEVICE AND METHOD OF PREDICTING USE INSTRUMENT, AND SURGERY ASSISTING ROBOT

(71) Applicant: Kawasaki Jukogyo Kabushiki Kaisha, Kobe (JP)

(72) Inventor: Yasuhiko Hashimoto, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 792 days.

(21) Appl. No.: 17/774,856

(22) PCT Filed: Nov. 5, 2020

(86) PCT No.: PCT/JP2020/041319
§ 371 (c)(1),
(2) Date: May 6, 2022

(87) PCT Pub. No.: WO2021/090870
PCT Pub. Date: May 14, 2021

(65) Prior Publication Data
US 2022/0387116 A1  Dec. 8, 2022

(30) Foreign Application Priority Data
Nov. 7, 2019 (JP) .................. 2019-202763

(51) Int. Cl.
*A61B 34/20* (2016.01)
*A61B 34/30* (2016.01)
*G06N 20/00* (2019.01)

(52) U.S. Cl.
CPC ............. *A61B 34/20* (2016.02); *A61B 34/30* (2016.02); *G06N 20/00* (2019.01); *A61B 2034/2065* (2016.02); *A61B 2034/305* (2016.02)

(58) Field of Classification Search
CPC .................. A61B 34/20; A61B 34/30; A61B 2034/2065; A61B 2034/305; A61B 34/25;
(Continued)

(56) References Cited

U.S. PATENT DOCUMENTS

2010/0174674 A1  7/2010 Unuma et al.
2014/0012793 A1* 1/2014 Park .................. G06F 3/017
                                                                 706/46
(Continued)

FOREIGN PATENT DOCUMENTS

| JP | 2001-112775 A | 4/2001 |
|---|---|---|
| JP | 2010-148604 A | 7/2010 |
| JP | 2019-139479 A | 8/2019 |
| WO | 2019/111512 A1 | 6/2019 |

OTHER PUBLICATIONS

Tian Zhou, et al., "Early Prediction for Physical Human Robot Collaboration in the Operating Room", arXiv:1709.09269v1, Sep. 26, 2017, 16 pages.
(Continued)

*Primary Examiner* — Pei Yong Weng
(74) *Attorney, Agent, or Firm* — XSENSUS LLP

(57) ABSTRACT

A use instrument predicting device includes a motion recognizing module that recognizes a motion of a surgeon during a surgical operation based on motion detection data that is obtained by detecting the surgeon's motion, a situation recognizing module that recognizes a surgery situation based on the motion recognized result of the motion recognizing module, and a predicting module that predicts at least one kind of surgical instrument to be used next by the surgeon out of a plurality of kinds of surgical instruments given beforehand, based on the situation recognized result of the situation recognizing module.

5 Claims, 6 Drawing Sheets

(58) Field of Classification Search
CPC .......... A61B 34/32; A61B 2017/00203; A61B 2017/00216; A61B 2034/2055; A61B 2034/254; A61B 2034/256; A61B 2034/258; A61B 2034/2072; G06N 20/00; G16H 40/20; G16H 40/63; G06F 3/167
See application file for complete search history.

(56) References Cited

U.S. PATENT DOCUMENTS

| | | |
|---|---|---|
| 2019/0223961 A1 | 7/2019 | Barral et al. |
| 2019/0272917 A1* | 9/2019 | Couture ................. G06N 20/00 |
| 2020/0085509 A1* | 3/2020 | Roh ....................... G16H 30/40 |
| 2020/0316778 A1* | 10/2020 | Desai .................... G16H 20/40 |

OTHER PUBLICATIONS

Tian Zhou, et al. "Spiking Neural Networks for Early Prediction in Human Robot Collaboration", arxiv.org, Cornell University Library, 201 Olin Library Cornell University Ithaca, NY 14853, Jul. 29, 2018 (Jul. 29, 2018), XP081252111.

Shoichi Nishio, et al. "Real-time Orthopedic Surgery Procedure Recognition Method with Video Images from Smart Glasses Using Convolutional Neural Network", 2018 IEEE International Conference on Systems, Man, and Cybernetics (SMC), IEEE, Oct. 7, 2018 (Oct. 7, 2018), pp. 379-384, XP033502654, DOI: 10.1109/SMC. 2018.00074 [retrieved on Jan. 16, 2019].

* cited by examiner

DEVICE AND METHOD OF PREDICTING USE INSTRUMENT, AND SURGERY ASSISTING ROBOT

CROSS-REFERENCE TO RELATED APPLICATIONS

The present application is based on PCT filing PCT/JP2020/041319, filed Nov. 5, 2020, which claims priority to Japanese Patent Application No. 2019-202763, filed Nov. 7, 2019, the entire contents of each are incorporated herein by reference

TECHNICAL FIELD

The present disclosure relates to a technique of predicting a surgical instrument suitable for a surgery situation during a surgical operation.

BACKGROUND ART

At surgical operation sites, a surgical instrument to be used by a surgeon is handed to the surgeon from a surgical room nurse (instrument handling nurse). Before a demand is verbally told from the surgeon, the nurse under a surgical operation predicts a surgical instrument to be used next based on the self experiences in consideration of the progress state of the surgery and the surgeon's motion, and prepares so that he/she can promptly pass it to the surgeon. Such an instrument handling work of the nurse is based on tacit knowledge, such as the surgeon's habit, operating pattern, etc.

In recent years, the technology for automatically recognizing a human motion by using sensor data obtained from a sensor apparatus etc. attracts the attention. For example, Patent Document 1 discloses a dynamic state recognition device which acquires information from a dynamic state sensor (wearable sensor) attached to a subject person, such as a worker, and recognizes a dynamic state item indicative of each state of the contents of the dynamic state performed by the subject person. This dynamic state recognition device detects the dynamic state of the subject by using the information from the dynamic state sensor, narrows down the dynamic state item based on the detected dynamic state, and performs recognition processing for the narrowed-down dynamic state item. Further, Patent Document 2 discloses a recognition device which acquires, from a camera, image data in which person's motion is projected, and predicts a motion recognized result (context). This recognition device has a selection engine and a plurality of different recognition engines. The selection engine automatically selects one or more recognition engines optimal for input data, and the motion recognized result which is derived by the selected recognition engine is outputted.

REFERENCE DOCUMENTS OF CONVENTIONAL ART

Patent Documents

[Patent Document 1] JP2010-148604A
[Patent Document 2] JP2019-139479A

DESCRIPTION OF THE DISCLOSURE

Problem(s) to be Solved by the Disclosure

Good or bad of the instrument handling work of the surgical room nurse as described above largely depends on the nurse's skill and skill level. Further, since the instrument handling nurse stays in a tensed state for a long period of time, or stays in a standing state, he/she becomes greatly fatigued physically as well as mentally.

Means for Solving the Problem(s)

The present inventors found out to perform by a computer at least a part of an instrument handling work, which is conventionally conducted by a surgical room nurse, that is, a selection of a surgical instrument suitable for a surgery situation. By this technique, the surgical instrument suitable for the surgery situation can be provided to the surgeon without depending on the nurse's skill and skill level. Further, it makes possible for a robot to pass the surgical instrument to the surgeon, which contributes to the reduction of fatigues of the surgical room nurse.

A use instrument predicting device according to one aspect of the present disclosure includes a motion sensing device that detects a motion of a surgeon during a surgical operation, a calculation module that has a learned model learned with a large number of teaching data in which input data including motion detection data obtained by the motion sensing device is associated with output data including at least one kind of surgical instrument predicted to be used next by the surgeon, and derives the output data to be recognized corresponding to the input data using the learned model, and an output device that outputs the output data.

Further, a use instrument prediction method according to one aspect of the present disclosure includes acquiring motion detection data that is obtained by detecting a motion of a surgeon during a surgical operation, the method includes, by using a learned model learned with a large number of teaching data in which input data including the motion detection data is associated with output data including at least one kind of surgical instrument predicted to be used next by the surgeon, deriving the output data to be recognized corresponding to the input data, and the method includes outputting the output data.

A use instrument predicting device according to one aspect of the present disclosure includes a motion recognizing module that recognizes a motion of a surgeon during a surgical operation based on motion detection data that is obtained by detecting the surgeon's motion, a situation recognizing module that recognizes a surgery situation based on the motion recognized result of the motion recognizing module, and a predicting module that predicts at least one kind of surgical instrument to be used next by the surgeon out of a plurality of kinds of surgical instruments given beforehand, based on the situation recognized result of the situation recognizing module.

Further, a use instrument prediction method according to one aspect of the present disclosure includes acquiring motion detection data that is obtained by detecting a motion of a surgeon during a surgical operation, recognizing the surgeon's motion based on the motion detection data, recognizing a surgery situation based on the recognized surgeon's motion, and predicting at least one kind of surgical instrument to be used next by the surgeon out of a plurality of kinds of surgical instruments given beforehand, based on the recognized surgery situation.

Furthermore, a surgery assisting robot according to one aspect of the present disclosure includes at least one manipulator arm, the use instrument predicting device, a robot control device that controls operation of the manipulator arm, and an instrument storage that accommodates a plurality of kinds of surgical instruments. The robot control device operates the manipulator arm so that the manipulator arm picks out at least one kind of surgical instrument to be used next by a surgeon predicted by the use instrument predicting device from the instrument storage, and transfers the surgical instrument to a given handing position. The given handing position may be a fixed position defined according to the contents of the surgical operation, a position defined beforehand according to the progress state of the surgical operation, or the surgeon's favorite handing position.

The motion recognizing module may recognize the surgeon's motion based on the motion detection data. For example, the motion detection data may be at least one of data detected by a dynamic state sensor attached to the surgeon and imaging data obtained by a camera which images the surgeon's motion. Further, the motion detection data may include surgeon identification information for identifying a surgeon. The motion recognizing module has a first learned model which has learned with a large number of first teaching data in which the motion detection data and the surgeon's motion which are accumulated are associated with each other. The motion recognizing module derives the surgeon's motion to be recognized corresponding to the motion detection data by using the first learned model.

The situation recognizing module recognizes the surgery situation based on situation detection data which includes the recognized result of the motion recognizing module (i.e., the surgeon's motion). The situation detection data may include the contents of the surgical operation, and a lapsed time of the surgical operation. The situation recognizing module has a second learned model which has learned with a large number of second teaching data in which the situation detection data and the surgery situation which are accumulated are associated with each other. The situation recognizing module derives the surgery situation to be recognized corresponding to the situation detection data by using the second learned model. Note that the surgery situation may include a progress of the surgical operation (surgical processes, such as incision, excision, and suture).

The predicting module predicts at least one kind of surgical instrument to be used next by the surgeon based on instrument prediction data including the situation recognized result of the situation recognizing module (i.e., the surgery situation). The instrument prediction data may include the surgeon identification information for identifying the surgeon. Based on the surgeon identification information, the surgeon's dominant hand, his/her favorite surgical instrument, and his/her favorite handing position can be identified. The predicting module has a third learned model which has learned with a large number of third teaching data in which the instrument prediction data and the kind of surgical instrument which are accumulated are associated with each other. The predicting module derives the kind of the surgical instrument corresponding to the instrument prediction data to be recognized using the third learned model. The third learned model may also derive the handing position according to the kind of surgical instrument. Note that the kinds of surgical instruments which are generally used for surgical operations are roughly divided into a needle holder, tweezers, a needle and thread, forceps, a hook, a retractor, etc. These major classifications of the surgical instruments are further finely classified depending on the shape of the tip end, the size and the use.

Effect of the Disclosure

According to the present disclosure, prediction of a surgical instrument suitable for a surgery situation, which is conventionally conducted by a surgical room nurse, can be performed automatically without depending on the nurse's skill and skill level.

MODES FOR CARRYING OUT THE DISCLOSURE

Figure 1:
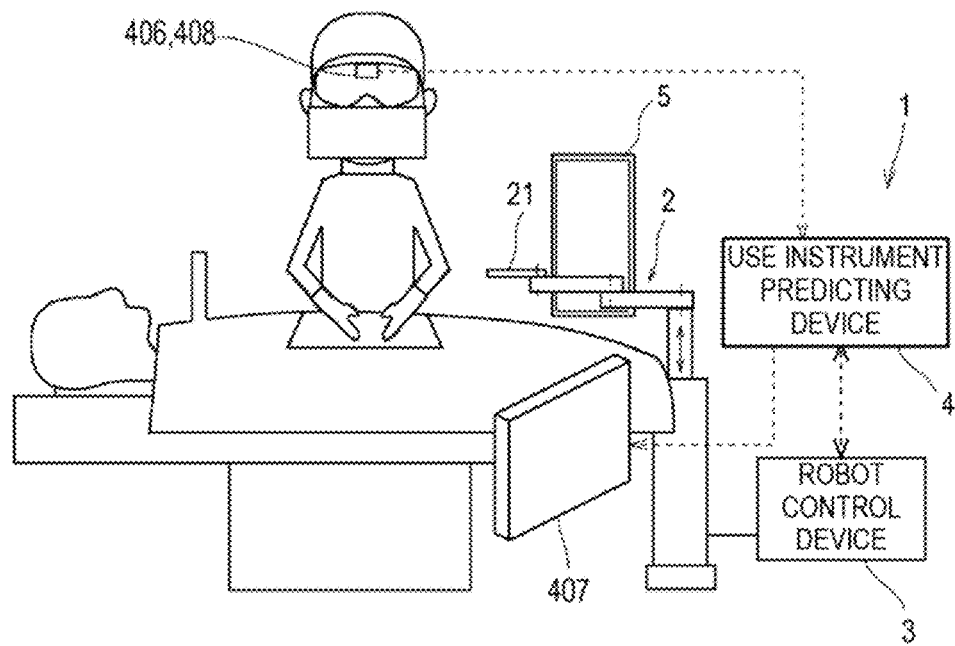
FIG. 1 is a view illustrating the entire configuration of a surgery assisting robot according to one embodiment of the present disclosure.

Next, one embodiment of the present disclosure is described with reference to the drawings. FIG. 1 is a view illustrating the entire configuration of a surgery assisting robot 1 according to one embodiment of the present disclosure. The surgery assisting robot 1 illustrated in FIG. 1 includes at least one manipulator arm 2, a robot control device 3, a use instrument predicting device 4, and an instrument storage 5. The instrument storage 5 stores a plurality of kinds of surgical instruments, which may be used for a surgery, in a sterile condition.

[Manipulator Arm 2]

The manipulator arm 2 is an articulated robotic arm having a plurality of joints. A hand 21 is attached to a distal-end part of the manipulator arm 2 as an end effector. The hand 21 is capable of grasping a surgical instrument. Although in this embodiment a horizontal articulated robotic arm is adopted as the manipulator arm 2, any kind of robotic arm can be adopted as long as the manipulator arm 2 is an articulated robotic arm. Further, the manipulator arm 2 may be installed by a surgical table, or may be suspended from the ceiling of a surgical room.

[Robot Control Device 3]

The robot control device 3 is provided with a computer, and by a processor performing a program, or a decryption and a calculation of various signals inputted from the use instrument predicting device 4, it controls the motion of the manipulator arm 2 and the motion of the hand 21, and outputs signals from various output ports.

Figure 2:
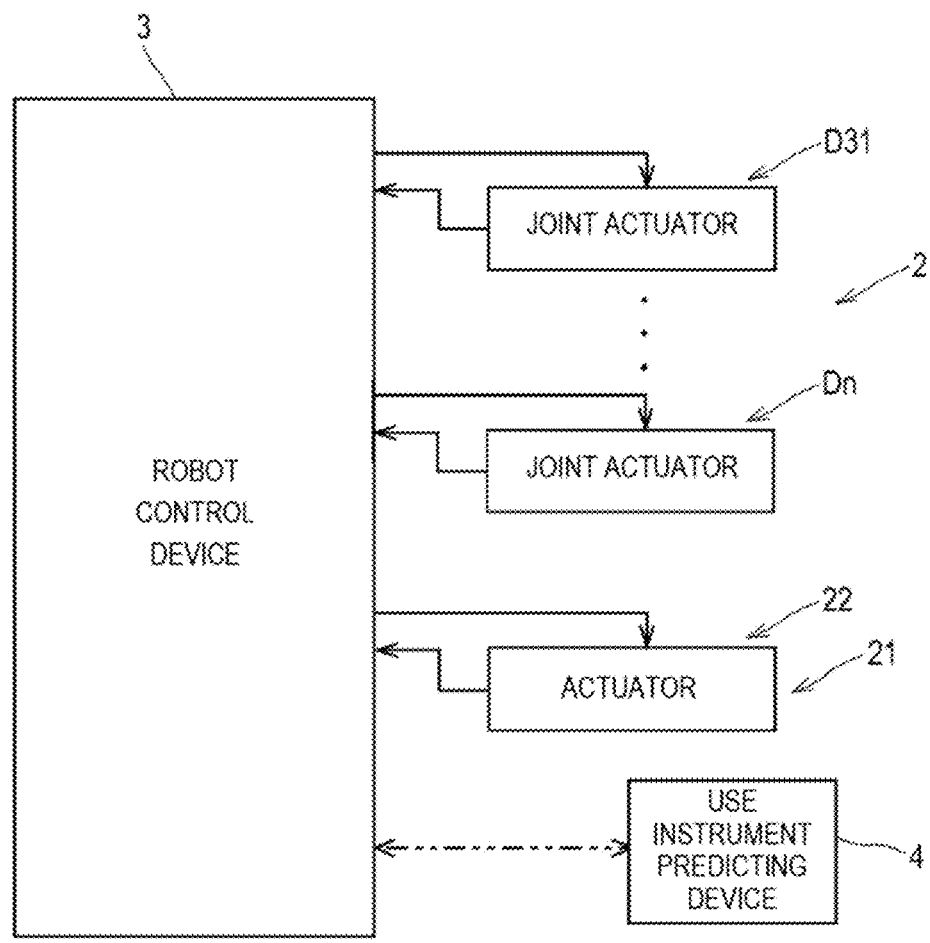
FIG. 2 is a schematic configuration diagram of a robot control device.

As illustrated in FIG. 2, the manipulator arm 2 is provided with joint actuators D31-Dn corresponding to the respective joints. For example, each of the joint actuators D31-Dn is comprised of a servomotor, a power transmission mechanism which transmits the power of the servomotor to the joint, a reduction gear which adjusts output torque of the servomotor and transmits it to the power transmission mechanism, and a rotational position sensor which detects a rotational position of the servomotor (none of them is illustrated). The robot control device 3 controls the position of a control point of the manipulator arm 2 (for example, a point on the hand 21) by acquiring a detection signal of the rotational position sensor for each of the joint actuators D31-Dn, and adjusting the output of the servomotor based on the detection signal. The hand 21 includes at least one actuator 22. The robot control device 3 controls the operation of the hand 21 by operating the actuator 22.

[Use Instrument Predicting Device 4]

Figure 3:
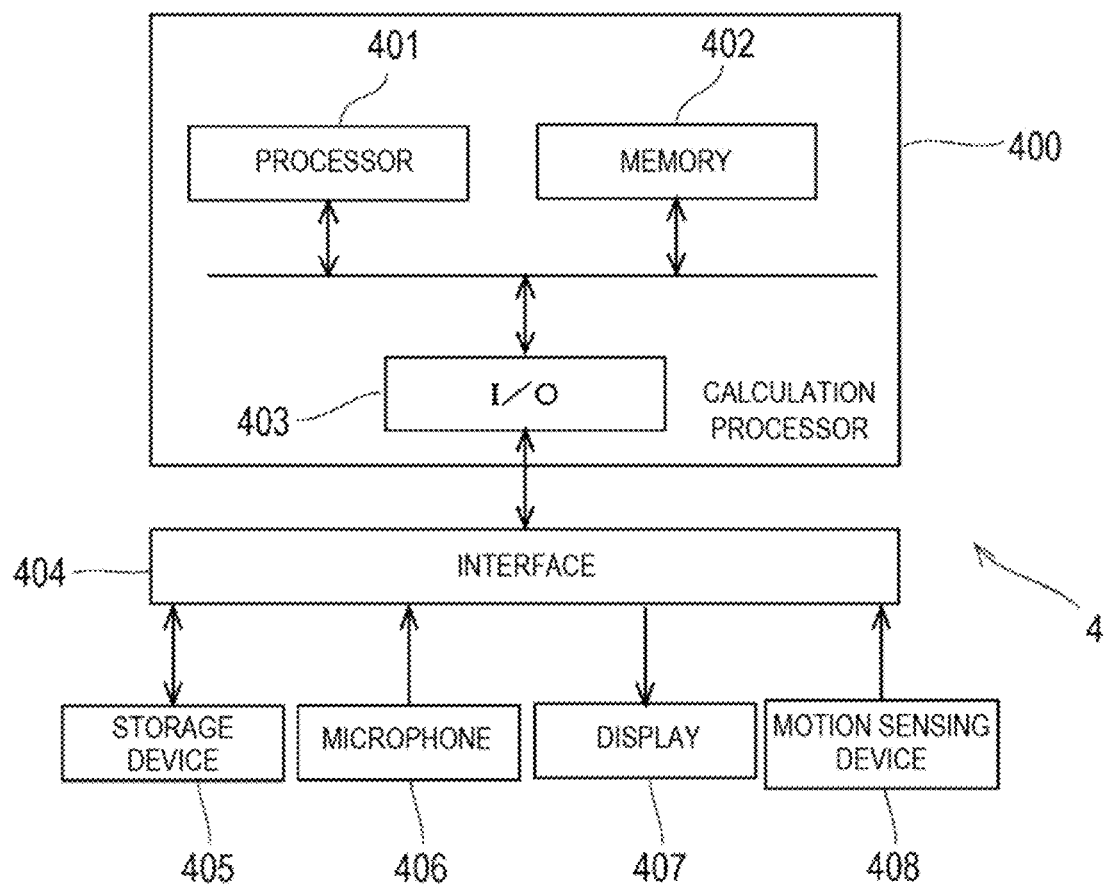
FIG. 3 is a schematic configuration diagram of a use instrument predicting device.

The use instrument predicting device 4 is provided with a calculation controller 400. Each functional part (described later) of the use instrument predicting device 4 may be comprised of at least one calculation controller 400, or two or more of a plurality of functional parts may be comprised of one calculation controller 400. As illustrated in FIG. 3, each calculation controller 400 of the use instrument predicting device 4 includes a processor 401, a memory 402 such as a ROM and a RAM, and an I/O part 403. The calculation controller 400 is connected with a storage device 405, a microphone 406, a display 407, and a motion sensing device 408 via an interface 404. The motion sensing device 408 may be at least one of a plurality of dynamic state sensors attached to a surgeon, and a camera which images the surgeon's motion and an affected part.

The calculation controller 400 may be provided with a sole processor 401 which performs a centralized control, or may be provided with a plurality of processors 401 which perform a distributed control. For example, the calculation controller 400 may be comprised of at least one of, or a combination of two or more of a computer, a personal computer, a microcontroller, a microprocessor, a PLD (Programmable Logic Device) such as a FPGA (Field-Programmable Gate Array), a PLC (Programmable Logic Controller), and a logical circuit. The memory 402 or the storage device 405 stores a basic program, a software program, etc. which are executed by the processor 401. By the processor 401 reading and executing the program, the calculation controller 400 realizes a function configured in the software program.

Figure 4:
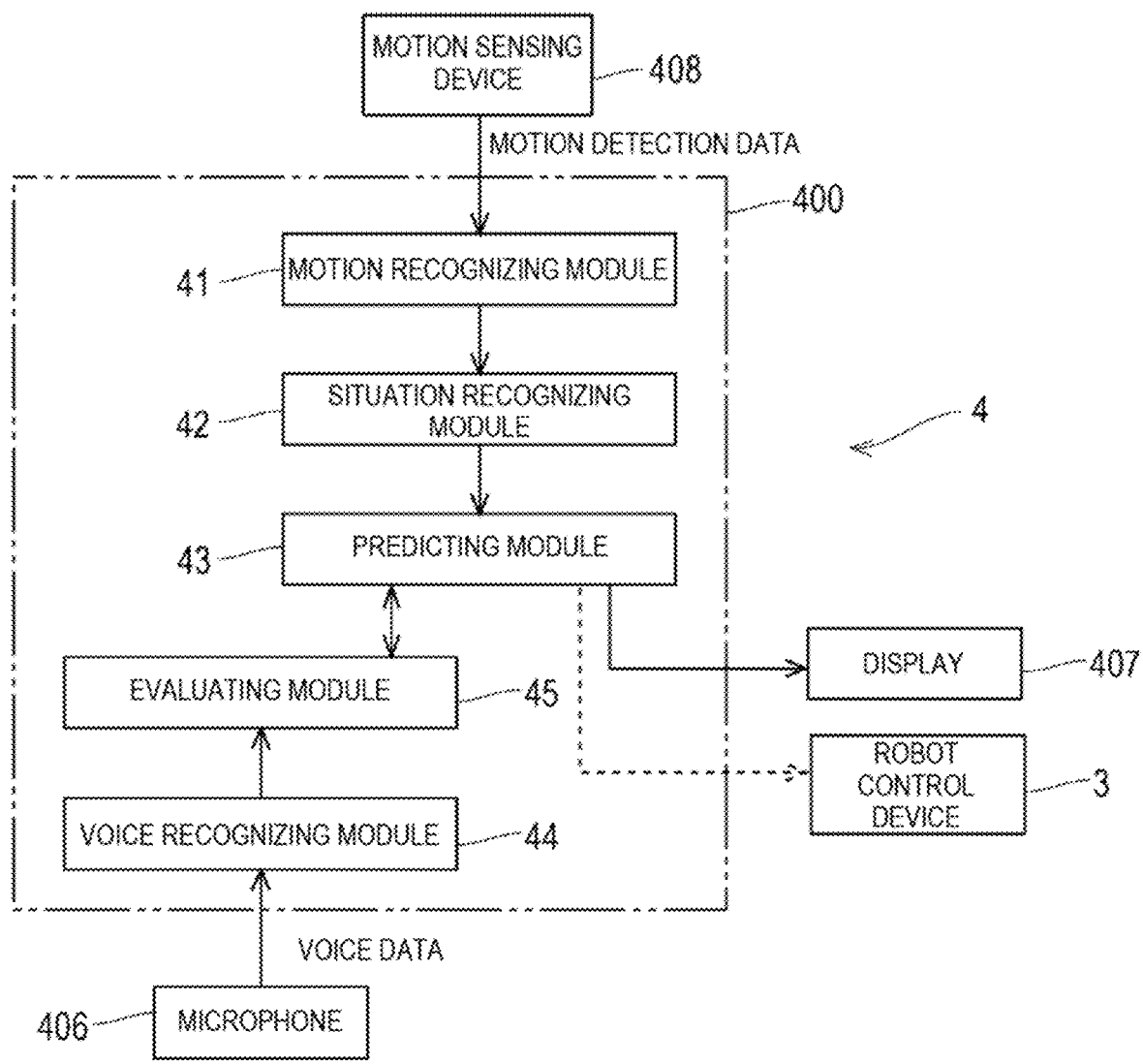
FIG. 4 is a functional block diagram of the use instrument predicting device.

As illustrated in FIG. 4, the use instrument predicting device 4 includes functional parts, such as a motion recognizing module 41, a situation recognizing module 42, a predicting module 43, a voice recognizing module 44, and an evaluating module 45. The use instrument predicting device 4 is also provided with a learning module (not illustrated) corresponding to each of the motion recognizing module 41, the situation recognizing module 42, and the predicting module 43.

[Motion Recognizing Module 41]

Figure 5:
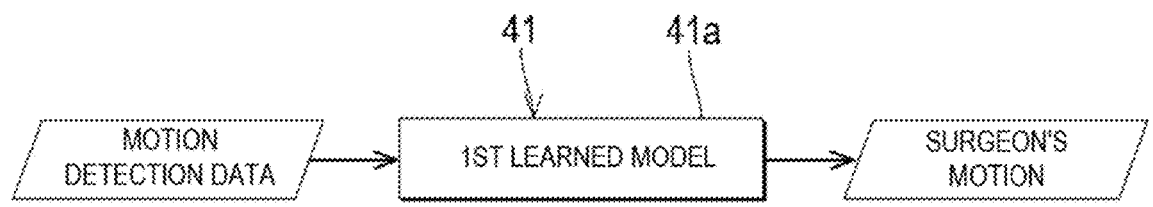
FIG. 5 is a view illustrating a flow of processing of a motion recognizing module.

As illustrated in FIG. 5, the motion recognizing module 41 recognizes a surgeon's motion based on motion detection data acquired from the motion sensing device 408. For example, the motion detection data may be at least one of data detected by the dynamic state sensor attached to the surgeon and imaging data obtained by the camera which images the surgeon's motion. Further, the motion detection data may include surgeon identification information for identifying a surgeon. The motion recognizing module 41 has a first learned model 41a which has learned with a large number of first teaching data in which the motion detection data and the surgeon's motion which are accumulated are associated with each other. The motion recognizing module 41 derives the surgeon's motion to be recognized corresponding to the motion detection data by using the first learned model 41a. For example, the motion recognizing module 41 can calculate a moving amount of the surgeon's specific part based on the motion detection data, and can recognize the surgeon's motion based on the moving amount. Note that the motion recognition technology has already been a known technology, and the motion recognizing module 41 can utilize the known motion recognition technology.

The learning module of the motion recognizing module 41 creates the first learned model 41a by using the machine learning technology. The learning module of the motion recognizing module 41 preprocesses the motion detection data to create the first teaching data. The preprocess includes at least one of various processings, such as a conversion of data format, a check of abnormality, an extraction of data, and a change of variable identifier or filename. The learning module of the motion recognizing module 41 learns a correlation between input data and output data by the machine learning. In this embodiment, the input data is the motion detection data and the output data is the surgeon's motion. The learning module of the motion recognizing module 41 performs supervised learning (class classification) as one example of the machine learning. Generally, the supervised learning is a technique in which a large number of known data sets (teaching data) comprised of input data and corresponding output data are given beforehand, and a feature which suggests a correlation between the input data and the output data is identified based on the teaching data using a learning algorithm to learn a correlation model for predicting necessary output data for new input data. This correlation model becomes the first learned model 41a. The first learned model 41a is stored in the storage device 405. The first teaching data in an early stage of learning is an accumulation of data set which includes the surgeon's motion detected by the motion sensing device 408 during an actual surgical operation, and the surgeon's motion which is given as a correct answer.

[Situation Recognizing Module 42]

Figure 6:
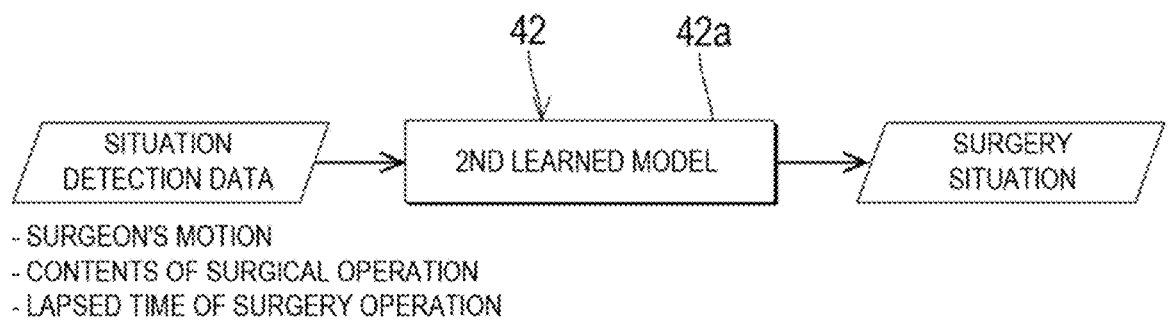
FIG. 6 is a view illustrating a flow of processing of a situation recognizing module.

As illustrated in FIG. 6, the situation recognizing module 42 recognizes a surgery situation based on situation detection data which includes the recognized result of the motion recognizing module 41 (i.e., the surgeon's motion). The situation detection data may include the contents of the surgical operation, and a lapsed time of the surgical operation. The situation recognizing module 42 has a second learned model 42a which has learned with a large number of second teaching data in which the situation detection data and the surgery situation which are accumulated are associated with each other. The situation recognizing module 42 derives the surgery situation to be recognized corresponding to the situation detection data by using the second learned model 42a. Note that the surgery situation may include a progress of the surgical operation (surgical processes, such as incision, excision, and suture).

The learning module of the situation recognizing module 42 creates the second learned model 42a by using the machine learning technology. The learning method of the learning module of the situation recognizing module 42 may be similar to that of the learning module of the motion recognizing module 41. The second teaching data in an early stage of learning is an accumulation of data set which includes the situation detection data obtained during an actual surgical operation, and the surgery situation which is given as a correct answer.

[Predicting Module 43]

Figure 7:
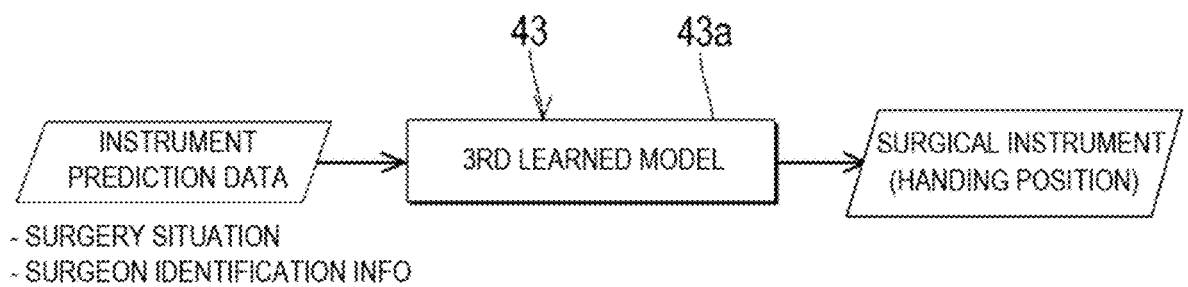
FIG. 7 is a view illustrating a flow of processing of a predicting module.

As illustrated in FIG. 7, the predicting module 43 predicts at least one kind of surgical instrument to be used next by the surgeon based on instrument prediction data including the situation recognized result of the situation recognizing module 42 (i.e., the surgery situation). The instrument prediction data may include the surgeon identification information for identifying the surgeon. Based on the surgeon identification information, the surgeon's dominant hand, his/her favorite surgical instrument, and his/her favorite handing position can be identified. The predicting module 43 has a third learned model 43a which has learned with a large number of third teaching data in which the instrument prediction data and the kind of surgical instrument which are accumulated are associated with each other. The predicting module 43 derives a kind of the surgical instrument corresponding to the instrument prediction data to be recognized using the third learned model 43a. Note that the kinds of surgical instruments which are generally used for surgical operations are roughly divided into a needle holder, tweezers, a needle and thread, forceps, a hook, the retractor, etc. These major classifications of the surgical instruments are further finely classified depending on the shape of the tip end, the size and the use.

The third learned model 43a may derive the handing position according to the kind of surgical instrument. The handing position may be a fixed position defined according to the contents of the surgical operation, a position defined beforehand according to the progress state of the surgical operation, or the surgeon's favorite handing position. Alternatively, the handing position may be identified by absolute coordinates, or may be identified as a position which opposes to the surgical table or the manipulator arm 2.

The learning module of the predicting module 43 creates the third learned model 43a using the machine learning technology. The learning method of the learning module of the predicting module 43 may be similar to that of the learning module of the motion recognizing module 41. The third teaching data in an early stage of learning is an accumulation of data set which includes the instrument prediction data obtained during an actual surgical operation, and the kind of surgical instrument which is given as a correct answer.

[Voice Recognizing Module 44]

The microphone 406 acquires a voice analog signal (i.e., voice), and converts it into a voice digital signal. The voice recognizing module 44 acquires the voice digital signal, and converts it into text data. For example, the voice recognizing module 44 converts the inputted voice into a voice wave, conducts an acoustic analysis of the voice wave to identify the phoneme, performs a matching of the row of the phoneme with a dictionary registered beforehand to convert it into a word, and outputs the converted sentence as text data. The speech recognition technology using machine learning is widely known, and the voice recognizing module 44 is constituted utilizing a known speech recognition technology.

[Evaluating Module 45]

The evaluating module 45 determines whether the prediction result by the predicting module 43 is correct. Processing of the evaluating module 45 will be described later.

[Surgical Operation Assisting Method]

Here, a surgical operation assisting method using the surgery assisting robot 1 is described. This surgical operation assisting method utilizes the use instrument prediction method according to this embodiment.

Figure 8:
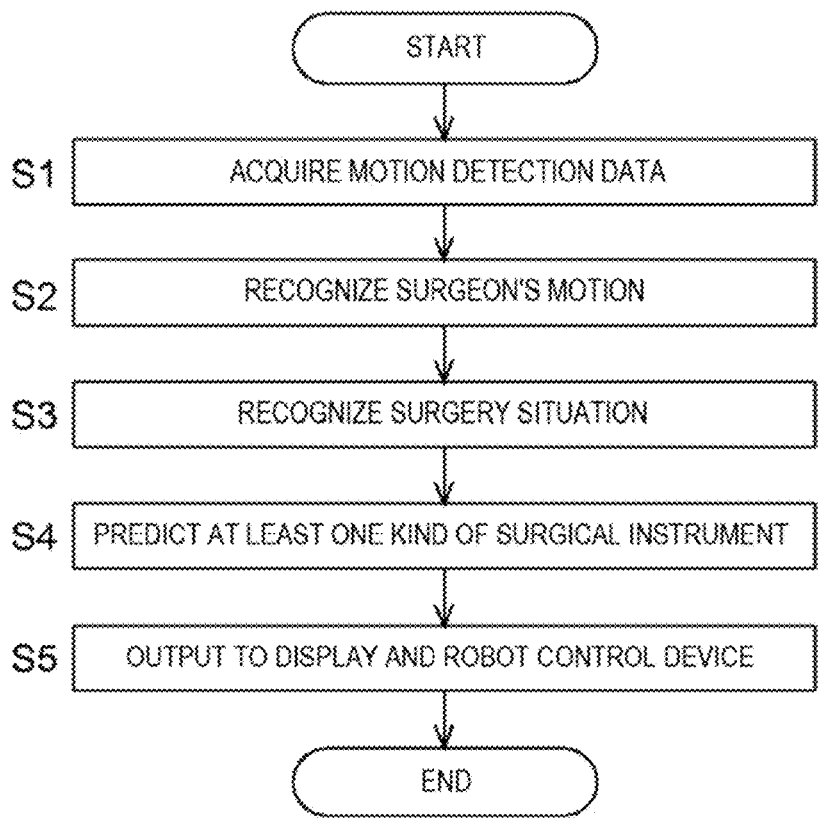
FIG. 8 is a flowchart of processing of the use instrument predicting device.
Figure 9:
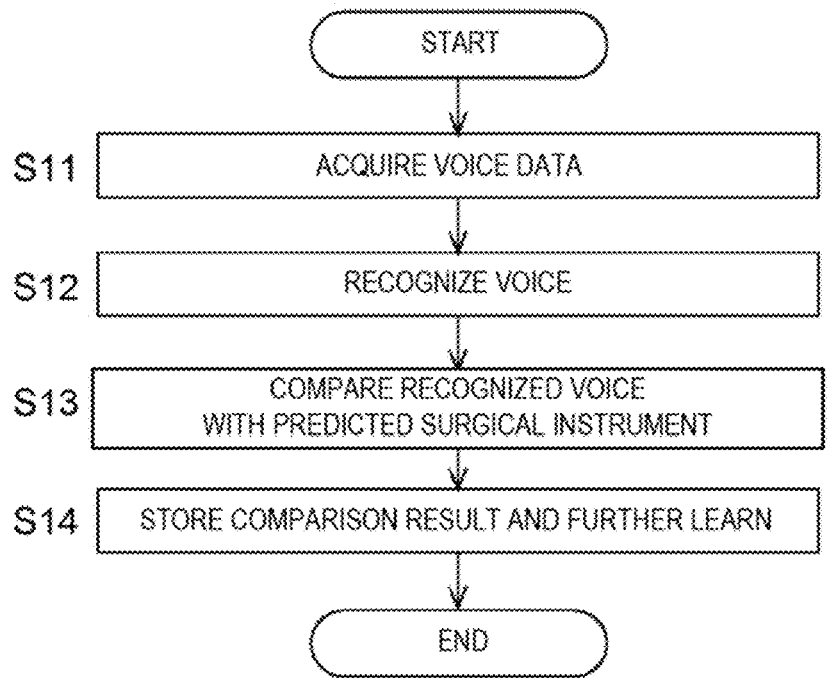
FIG. 9 is a flowchart of the processing of the use instrument predicting device.

FIGS. 8 and 9 are flowcharts of processing of the use instrument predicting device 4. As illustrated in FIG. 8, the use instrument predicting device 4 acquires the motion detection data which is obtained by detecting the surgeon's motion under a surgical operation from the motion sensing device 408 (Step S1).

Next, the motion recognizing module 41 of the use instrument predicting device 4 recognizes the surgeon's motion based on the motion detection data (Step S2). Then, the situation recognizing module 42 of the use instrument predicting device 4 recognizes the surgery situation based on the motion recognized result (i.e., the surgeon's motion) of the motion recognizing module 41 (Step S3). Further, the predicting module 43 of the use instrument predicting device 4 predicts at least one kind of surgical instrument to be used next by the surgeon out of a plurality of kinds of surgical instruments given beforehand, based on the situation recognized result (i.e., the surgery situation) of the situation recognizing module 42 (Step S4).

The use instrument predicting device 4 outputs the prediction result of the surgical instrument to the display 407 (Step S5). The display 407 is disposed at a position where the surgeon inside the surgical room can view. The surgeon can visually recognize the information on the surgical instrument which will be provided next, which is displayed on and outputted to the display 407.

Further, the use instrument predicting device 4 outputs the prediction result of the surgical instrument to the robot control device 3 (Step S5). The robot control device 3, which received the prediction result of the surgical instrument, operates the manipulator arm 2 so that it picks out at least one kind of predicted surgical instrument which will be used next by the surgeon from the instrument storage 5, and then stands by at a standby position.

The surgeon utters voice in order to demand a surgical instrument to be used next. For example, the surgeon utters as "scalpel." This voice is collected by the microphone 406 and transmitted to the use instrument predicting device 4.

As illustrated in FIG. 9, the voice recognizing module 11 of the use instrument predicting device 4 acquires the voice data from the microphone 406 (Step S11), and performs the speech recognition (Step S12). The voice data is converted into the voice text data by the speech recognition.

The evaluating module 45 of the use instrument predicting device 4 compares the voice text data (i.e., the voice recognized) with the information on the surgical instrument predicted by the predicting module 43, and determines a match or a non-match (Step S13). The use instrument predicting device 4 stores the determination result, creates new teaching data including the motion detection data, the surgical instrument predicted based on the motion detection data, and the determination result, and causes the learned models 41a, 42a, and 43a to further learn (Step S14).

If determined matched at Step S13, the use instrument predicting device 4 outputs an enabling signal to the robot control device 3. The robot control device 3 which received the enabling signal operates the manipulator arm 2 so that the manipulator arm 2 moves from the standby position to the handing position. Therefore, the surgical instrument demanded by the surgeon can be provided promptly and correctly.

On the other hand, if determined non-matched at Step S13, the use instrument predicting device 4 outputs the prediction result of at least one surgical instrument which is derived from the voice text data, and an enabling signal to the robot control device 3. The robot control device 3 which received the prediction result of the surgical instrument operates the manipulator arm 2 so that the manipulator arm 2 picks out at least one kind of predicted surgical instrument to be used next by the surgeon from the instrument storage 5, and moves it to the handing position. Therefore, the surgical instrument demanded by the surgeon can be provided correctly.

As described above, the use instrument predicting device 4 according to this embodiment includes the motion recognizing module 41 which recognizes the surgeon's motion during a surgical operation based on the motion detection data which is obtained by detecting the surgeon's motion, the situation recognizing module 42 which recognizes the surgery situation based on the motion recognized result of the motion recognizing module 41, and the predicting module 43 which predicts at least one kind of surgical instrument to be used next by the surgeon out of the plurality of kinds of surgical instruments given beforehand, based on the situation recognized result of the situation recognizing module 42.

Moreover, the use instrument prediction method according to this embodiment includes the steps of acquiring the motion detection data which is obtained by detecting the surgeon's motion during a surgical operation, recognizing the surgeon's motion based on the motion detection data, recognizing the surgery situation based on the recognized surgeon's motion, and predicting at least one kind of surgical instrument to be used next by the surgeon out of the plurality of kinds of surgical instruments given beforehand, based on the recognized surgery situation.

The surgery assisting robot 1 according to this embodiment includes the use instrument predicting device 4, the at least one manipulator arm 2, the robot control device 3 which controls the operation of the manipulator arm 2, and the instrument storage 5 which accommodates the plurality of kinds of surgical instruments. The robot control device 3 operates the manipulator arm 2 so that the manipulator arm 2 picks out from the instrument storage 5 the at least one kind of surgical instrument to be used next by the surgeon, which is predicted by the use instrument predicting device 4, and transfers it to the given handing position.

According to the use instrument predicting device 4, the method, and the surgery assisting robot 1, which are described above, the prediction of the surgical instrument suitable for the surgery situation, which is conventionally conducted by the surgical room nurse, can be performed automatically without depending on the nurse's skill and skill level.

In the use instrument predicting device 4, the motion recognizing module 41 includes the first learned model 41a learned with the large number of first teaching data in which the motion detection data is associated with the surgeon's motion, and derives the surgeon's motion to be recognized corresponding to the motion detection data using the first learned model 41a.

In the use instrument predicting device 4, the situation recognizing module 42 includes the second learned model 42a learned with the large number of second teaching data in which the situation detection data including the motion recognized result is associated with the surgery situation, and derives the surgery situation to be recognized corresponding to the situation detection data using the second learned model 42a.

In the use instrument predicting device 4, the predicting module 43 includes the third learned model 43a learned with the large number of third teaching data in which the instrument prediction data including the situation recognized result is associated with the kind of surgical instrument, and derives the kind of surgical instrument to be recognized corresponding to the instrument prediction data using the third learned model 43a.

Further, in the use instrument predicting device 4, the predicting module 43 derives the handing position which is the position where the predicted surgical instrument is passed to the surgeon.

According to the use instrument predicting device 4 having the above configuration, the surgical instrument to be demanded next by the surgeon can be estimated correctly.

Although the suitable embodiment of the present disclosure is described above, changes of the concrete structure of the above embodiment and/or the details of the function may be encompassed within the scope of the present disclosure, without departing from the spirit of the present disclosure. The configurations of the use instrument predicting device 4 and the surgery assisting robot 1 having the same can be changed as follows, for example.

Figure 10:
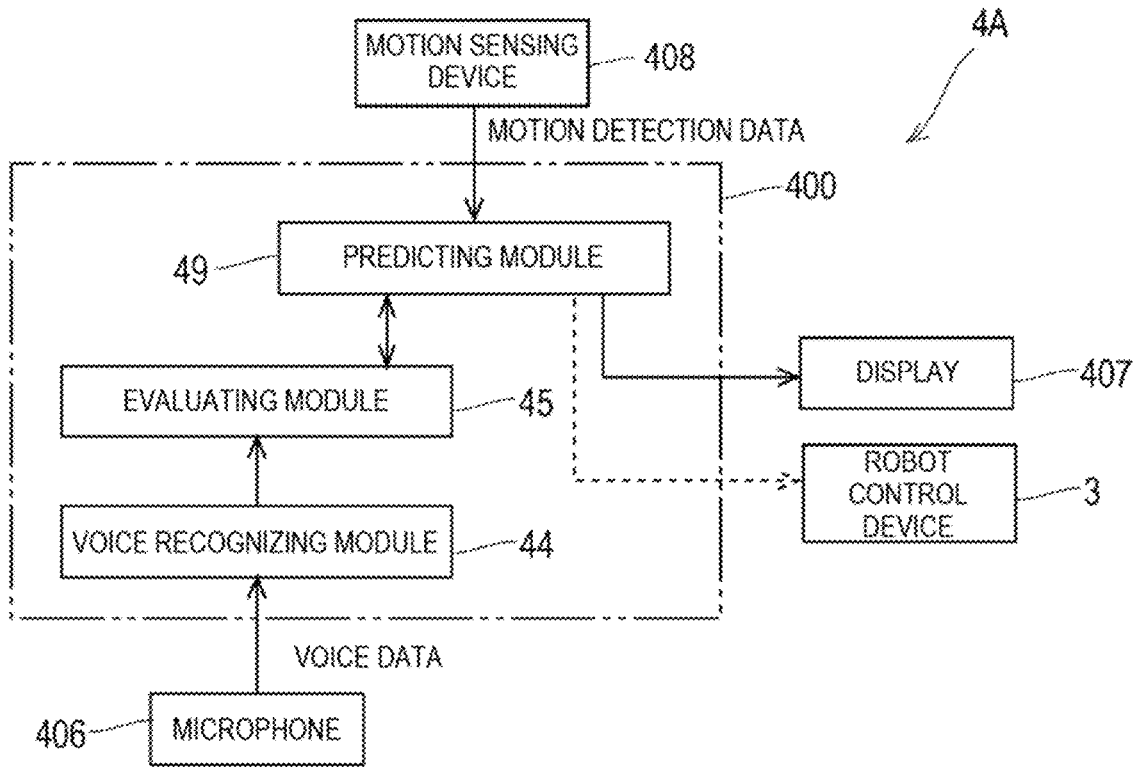
FIG. 10 is a functional block diagram of a use instrument predicting device according to Modification 1.
Figure 11:
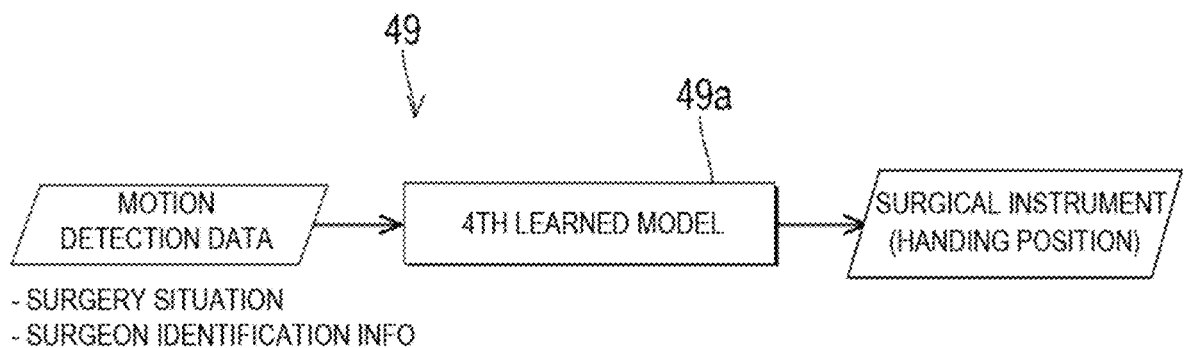
FIG. 11 is a view illustrating a flow of processing of the use instrument predicting device according to Modification 1.

For example, in the above embodiment, the calculation controller 400 of the use instrument predicting device 4 includes the first to third learned models 41a, 42a, and 43a. However, instead of the motion recognizing module 41, the situation recognizing module 42, and the predicting module 43 provided with the learned models 41a, 42a, and 43a, respectively, as illustrated in FIGS. 10 and 11, a calculation controller 400 of a use instrument predicting device 4A may be provided with a calculation module 49 having a fourth learned model 49a.

The fourth learned model 49a derives output data including at least one kind of surgical instrument which is predicted to be used next by the surgeon, from the input data including the motion detection data. In this case, for example, the motion detection data may be at least one of the data detected by the dynamic state sensor attached to the surgeon, and the imaging data obtained by the camera which images the surgeon's motion. Further, the input data may further include at least one of the surgeon identification information for identifying the surgeon, the contents of the surgical operation, and the lapsed time of the surgical operation. Moreover, the output data may further include the handing position which is the position where at least one kind of predicted surgical instrument is passed to the surgeon.

The calculation module 49 includes the learning module. The learning module of the calculation module 49 establishes the fourth learned model 49a using the machine learning technology. The learning module of the use instrument predicting device 4 preprocesses the motion detection data to create the fourth teaching data. The preprocess includes at least one of various processings, such as the conversion of the data format, the check of the abnormality, the extraction of the data, and the change of the variable identifier and the filename. The learning module of the calculation module 49 learns the correlation between the input data and the output data by the machine learning. For example, this machine learning is the supervised learning (class classification), and the learning algorithm is suitably adopted according to the input/output data. The learning module of the calculation module 49 learns the correlation model for predicting the necessary output data to the new input data by receiving beforehand the large number of known data sets (teaching data) of the input data and the corresponding output data, and identifying the feature which suggests the correlation between the input data and the output data based on the teaching data using the learning algorithm. This correlation model becomes the fourth learned model 49a. The fourth learned model 49a is stored in the storage device 405. The fourth teaching data in the early stage of the learning is the accumulation of data set which includes the surgeon's motion detected by the motion sensing device 408 during the actual surgical operation, and the kind of surgical instrument which is given as the correct answer.

The use instrument prediction method performed by the calculation controller 400 of the use instrument predicting device 4A having the above configuration includes the steps of acquiring the motion detection data which is obtained by detecting the surgeon's motion during the surgical operation, from the motion sensing device 408, deriving the output data to be recognized corresponding to the input data, using the learned model 49a which has learned with the large number of teaching data in which the input data including the motion detection data is associated with the output data including at least one kind of surgical instrument predicted to be used next by the surgeon, and outputting the output data to the robot control device 3, the display 407, etc. Further, similar to the learned models 41a, 42a, and 43a described above, the learning module of the calculation module 49 creates the new teaching data which includes the motion detection data, the surgical instrument predicted based on the motion detection data, and the determination result in the use instrument prediction processing to cause the fourth learned model 49a to further learn.

In the above embodiment, when at least one kind of surgical instrument which is predicted by the use instrument predicting device 4 differs from the surgical instrument demanded by the surgeon, the manipulator arm 2 goes to the instrument storage 5 to again take out the demanded surgical instrument, and carries it to the handing position. However, the manipulator arm 2 may return the surgical instrument to the instrument storage 5 while the demanded surgical instrument may be handed to the surgeon from a nurse. Further, when the handing position differs from the position demanded by the surgeon, the nurse may move the manipulator arm 2 to the correct handing position, the robot control device 3 may then acquire the correct handing position, and the use instrument predicting device 4 may learn the position. In order for the nurse to be able to move the manipulator arm 2, the manipulator arm 2 may be provided with a hand guide button. The manipulator aim 2 serves as a hand guide robot while the hand guide button is pushed, and the robot control device 3 controls the operation of the manipulator arm 2 so that the manipulator arm 2 is freely movable by an external force given by the nurse.

Although in the above embodiment the learned models 41a, 42a, and 43a provided to the use instrument predicting device 4 learn every time the series of prediction processings is finished, the additional learning may be performed after a plurality of prediction processings are finished and a certain amount of teaching data is accumulated.

DESCRIPTION OF REFERENCE CHARACTERS

1: Surgery Assisting Robot
2: Manipulator Arm
3: Robot Control Device
4: Use Instrument Predicting Device
5: Instrument Storage
400: Calculation Controller
41: Motion Recognizing Module
41a, 42a, 43a, 49a: Learned Model
42: Situation Recognizing Module
43: Predicting Module
49: Calculation Module

The invention claimed is:

1. A use instrument predicting device, comprising:
a motion sensor that detects a motion of a surgeon during a surgical operation;
calculation circuitry that includes:
  a first learned model to derive a motion of a surgeon during a surgical operation based on the detected motion, the first learned model learned with first teaching data in which the detected motion is associated with the surgeon's motion,
  a second learned model to derive a surgery situation, the second learned model learned with second teaching data including the surgeon's motion derived from the first learned model, contents of the surgical operation and lapsed time of the surgical operation,
  a third learned model to predict at least one kind of surgical instrument to be used next by the surgeon out of a plurality of kinds of surgical instruments given beforehand, the third learned model learned with third teaching data including the surgery situation derived from the second learned model and surgeon identification information,
wherein the third learned model also derives a handing position according to the predicted at least one kind of surgical instrument, the handing position being defined according to contents of the surgical operation, a position defined beforehand according to a progress state of the surgical operation, or the surgeon's favorite handing position, the handing position being a position where the predicted at least one kind of surgical instrument is passed to the surgeon; and
output circuitry configured to output the output data.

2. A use instrument predicting device, comprising:
motion recognizing circuitry configured to derive a motion of a surgeon during a surgical operation based on motion detection data that is obtained by detecting the surgeon's motion;
situation recognizing circuitry configured to derive a surgery situation based on the motion recognized result of the motion recognizing circuitry; and
predicting circuitry configured to predict at least one kind of surgical instrument to be used next by the surgeon out of a plurality of kinds of surgical instruments given beforehand, based on the situation recognized result of the situation recognizing circuitry,
wherein the motion recognizing circuitry has a first learned model learned with first teaching data in which the motion detection data is associated with the surgeon's motion, and the first learned model derives the surgeon's motion to be recognized corresponding to the motion detection data, by using the first learned model,
wherein the situation recognizing circuitry has a second learned model learned with second teaching data including the surgeon's motion derived from the first learned model, contents of the surgical operation and lapsed time of the surgical operation, and the second learned model derives the surgery situation to be recognized corresponding to the situation detection data, by using the second learned model,
wherein the predicting circuitry has a third learned model learned with third teaching data including the surgery situation derived from the second learned model and surgeon identification information, and the third learned model derives the kind of surgical instrument to be recognized corresponding to the instrument prediction data, by using the third learned model, and wherein the third learned model also derives a handing position according to the predicted at least one kind of surgical instrument, the handing position being defined according to contents of the surgical operation, a position defined beforehand according to a progress state of the surgical operation, or the surgeon's favorite handing position, the handing position being a position where the predicted at least one kind of surgical instrument is passed to the surgeon.

3. A surgery assisting robot, comprising:

the use instrument predicting device of claim 1;

at least one manipulator arm;

robot control circuitry that controls operation of the manipulator arm; and an instrument storage that accommodates a plurality of kinds of surgical instruments, wherein the robot control circuitry operates the manipulator arm so that the manipulator arm picks out at least one kind of surgical instrument to be used next by a surgeon predicted by the use instrument predicting device from the instrument storage, and transfers the surgical instrument to a given handing position.

4. A use instrument prediction method, comprising the steps of:

acquiring motion detection data that is obtained by detecting a motion of a surgeon during a surgical operation;

deriving, by a first learned model, a motion of a surgeon during a surgical operation based on the motion detection data, the first learned model learned with first teaching data in which the motion detection data is associated with the surgeon's motion, deriving, by a second learned model, a surgery situation, the second learned model learned with second teaching data including the surgeon's motion derived from the first learned model, contents of the surgical operation and lapsed time of the surgical operation, predicting, by a third learned model, at least one kind of surgical instrument to be used next by the surgeon out of a plurality of kinds of surgical instruments given beforehand, the third learned model learned with third teaching data including the surgery situation derived from the second learned model and surgeon identification information, wherein the third learned model also derives a handing position according to the predicted at least one kind of surgical instrument, the handing position being defined according to contents of the surgical operation, a position defined beforehand according to a progress state of the surgical operation, or the surgeon's favorite handing position, the handing position being a position where the predicted at least one kind of surgical instrument is passed to the surgeon; and outputting the output data.

5. A use instrument prediction method, comprising the steps of:

acquiring motion detection data that is obtained by detecting a motion of a surgeon during a surgical operation;

deriving, using a first learned model, the surgeon's motion based on the motion detection data, the first learned model being learned with first teaching data in which the motion detection data is associated with the surgeon's motion;

deriving, using a second learned model, a surgery situation based on the recognized surgeon's motion, the second learned model learned with second teaching data including the surgeon's motion derived from the first learned model, contents of the surgical operation and lapsed time of the surgical operation; and predicting, using a third learned model, at least one kind of surgical instrument to be used next by the surgeon out of a plurality of kinds of surgical instruments given beforehand, based on the recognized surgery situation, the third learned model learned with third teaching data including the surgery situation derived from the second learned model and surgeon identification information, wherein the third learned model also derives a handing position according to the predicted at least one kind of surgical instrument, the handing position being defined according to contents of the surgical operation, a position defined beforehand according to a progress state of the surgical operation, or the surgeon's favorite handing position, the handing position being a position where the predicted at least one kind of surgical instrument is passed to the surgeon.

* * * * *